US006556867B1

(12) United States Patent
Kohls

(10) Patent No.: US 6,556,867 B1
(45) Date of Patent: Apr. 29, 2003

(54) APPARATUS AND METHOD TO POWER A MEDICAL DEVICE USING STORED MECHANICAL POWER

(75) Inventor: Mark R. Kohls, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/414,468

(22) Filed: Oct. 7, 1999

(51) Int. Cl.$^7$ ................................................ A61N 1/39
(52) U.S. Cl. .............................. 607/35; 607/5; 607/33
(58) Field of Search .......................... 607/2, 4, 5, 9, 607/33, 34, 35, 61

(56) References Cited

U.S. PATENT DOCUMENTS

| | | | | |
|---|---|---|---|---|
| 1,913,595 A | * | 6/1933 | Hyman et al. .................. 607/10 |
| 3,826,265 A | * | 7/1974 | Giori et al. ................... 128/419 |
| 3,913,588 A | * | 10/1975 | Klomp ......................... 128/419 |
| RE30,366 E | * | 8/1980 | Rasor et al. ............... 128/419 P |
| 4,510,935 A | * | 4/1985 | Spencer ....................... 128/419 |
| 5,285,779 A | * | 2/1994 | Cameron et al. ............... 607/5 |
| 5,472,453 A | | 12/1995 | Alt |
| 5,507,781 A | * | 4/1996 | Kroll et al. ..................... 607/7 |
| 5,662,692 A | | 9/1997 | Paspa et al. |
| 5,880,532 A | * | 3/1999 | Stopher ......................... 290/1 |
| 5,919,212 A | * | 7/1999 | Olson et al. .................... 607/5 |
| 5,932,943 A | | 8/1999 | Werner et al. |

OTHER PUBLICATIONS

John Hutchinson, "How the clockwork radio works," <http://www.britishcouncil.org/science/science/personalities/text/ukperson/baylis3.htm>, download date Aug. 3, 2000.

"Simply Radios," <http://simplyradios.com/acatalog/Home_Lanterns_122.html>, download date Aug. 3, 2000.

* cited by examiner

Primary Examiner—Jeffrey R. Jastrzab
Assistant Examiner—Frances P. Oropeza
(74) Attorney, Agent, or Firm—Foley & Lardner; Peter J. Vogel; Michael A. Della Penna

(57) ABSTRACT

A cardiac defibrillator for discharging an electrical charge into a patient includes a device for storing mechanical energy, a generator, a capacitor, a charging circuit, a patient interface, an input device, and a control unit. The generator converts mechanical energy stored in the mechanical energy storage device into electrical energy. The charging circuit transfers the electrical energy to the capacitor, wherein the electrical energy is stored in the capacitor. The patient interface provides an electrical path for discharging the electrical energy stored in the capacitor into the patient. The input device is configured to generate a discharge signal. The control unit controls the discharge of the electrical energy into the patient in response to the discharge signal. The mechanical-to-electrical energy converter assembly can also be used to power other medical devices that conventionally run on batteries or AC power line sources.

35 Claims, 2 Drawing Sheets

APPARATUS AND METHOD TO POWER A MEDICAL DEVICE USING STORED MECHANICAL POWER

BACKGROUND OF THE INVENTION

This invention relates to medical devices and particularly to powering medical devices with electrical energy converted from mechanical energy.

Conventional electrical medical devices receive their electrical energy from either a direct power line or from a battery. Such medical devices include cardiac defibrillators, electrocardiographs (stationary recorders and ambulatory "Holter" or event recorders), transport monitoring equipment and other electrical medical devices.

One such medical device is a cardiac defibrillator, which discharges electrical energy into a patient to restore a normal rhythmic heartbeat. The normal rhythmic heartbeat can be disrupted for several reasons. For example, cardiac arrest occurs when there is a sudden cessation of a heartbeat, or when there is a loss of effective pumping of blood by the heart. Typically, cardiac arrest is caused by arrhythmias, which abruptly cease circulation throughout the body and vital organs. Without rapid resuscitation, victims of cardiac arrest become permanently injured or die. Typically, arrhythmias are caused by disturbances in the electrical conduction mechanism of the heart. One type of arrhythmia, fibrillation, occurs where the electrical activity causes the heart to twitch rapidly, replacing the normal rhythmic heartbeat. Defibrillation is the process of restoring the heart to its normal rhythmic heartbeat. Typically, defibrillation occurs when a defibrillator operator, such as a physician, paramedic or other emergency care personnel, administers one or more electric charges or shocks to the patient using a defibrillator. Defibrillators are either implantable, meaning the device operates in vivo, or external, meaning the device acts from outside the body.

Cardiac defibrillators include circuitry, a capacitor, and a power source. The power source for conventional defibrillators is either an AC power source (e.g., from an electric power line) or a battery. The circuitry of the conventional defibrillator passes electrical energy from the power source to the capacitor. Then when the defibrillator operator instructs the defibrillator to deliver the shock, the stored charge of the capacitor is discharged into a patient to provide a therapeutic shock.

FIG. 1 shows the general arrangement of a conventional defibrillator 10. Conventional defibrillator 10 includes a battery 20, a control unit 30, a charging circuit 40, a capacitor 50, a patient interface 60, and a printer 70.

Battery 20 supplies electrical energy to control unit 30 and to capacitor 50 through charging circuit 40. If battery 20 is rechargeable, defibrillator 10 typically also includes an external battery charger 25.

Control unit 30 controls the operation of defibrillator 10. When the defibrillator operator instructs defibrillator 10 to deliver the charge to the patient, control unit 30 signals capacitor 50 to pass the stored charge to the patient through patient interface 60. Control unit 30 may also include a display (not shown) for the defibrillator operator to view (such as a conventionally known backlit LCD or the like).

Charging circuit 40 transfers the electrical energy from battery 20 to capacitor 50. Generally, charging circuits include a power conditioning circuit (not shown), which receives power from battery 20, and a transformer or rectifier circuit (not shown) coupled to the conditioning circuit and intermediate the power conditioning circuit and capacitor 50. Charging circuit 40 increases the voltage supplied from the battery 20 and outputs the increased voltage to the capacitor 50. Capacitor 50 holds the charge until it is delivered or discharged into a patient through patient interface 60.

Capacitor 50 and control unit 30 are electrically coupled to patient interface 60. Patient interface 60 usually includes either pads or paddles (not shown) that are placed in physical contact with the patient by the defibrillator operator. The paddles may range in size according to the expected use (e.g., pediatric to adult patients) and preferably include charge/shock and printer buttons. For example, the paddles may range in size from approximately 17 $cm^2$ (or smaller) to approximately 80 $cm^2$ in area (or larger). The pads include an adapter cable for adult and pediatric pads. When pads are used, the buttons for charge/shock and printer are located elsewhere on the defibrillator (e.g., on control unit 30).

Printer 70 is electrically coupled to control unit 30, and is used to output rhythm strips and textual information before, during, and after operation.

Generally, conventional defibrillators receive their electric energy from either an AC source (such as a power line) or a battery (e.g., disposable or rechargeable). When power line electricity is used, the use of the defibrillator is limited to situations where line power is available and reliable. Line power is not available or reliable when, for example, there are blackouts, brown outs, natural disasters, or the like. Battery powered defibrillators are mobile but limited in other ways and thus have several disadvantages. For example, after a defibrillator has been used, or after a set maintenance interval, the battery must either be replaced or recharged by the external battery charger. After numerous recharges by the battery charger, a rechargeable battery should be replaced as its effective charge retention diminishes. Also, a battery adds significant size and weight to a battery-operated device's overall configuration. In addition, batteries have a limited power supply, which requires defibrillator operators to charge and monitor battery energy levels. When the defibrillator is a mobile unit, battery charging or battery replacement may not be an option, due to a lack of a power source for recharging, or for a lack of spare batteries. Further, while a defibrillator sits for an extended period of time, the batteries gradually lose their energy supply, or degrade.

Thus, there is a long felt need for a medical device (such as a cardiac defibrillator) that is mobile and does not rely on a battery or line power as a power source. A medical device that receives its energy from a source of mechanical energy would be advantageous in various applications. For example, conventional medical devices that are operated by hospital personnel ("in-hospital") or by trained personnel before the patient can be brought to the hospital, e.g., by paramedics ("pre-hospital") require a reliable power source. Maintenance errors, or malfunctioning or degraded power sources, may all adversely affect the power source reliability. For pre-hospital and in-hospital uses, errors that occur during monitoring and maintenance of battery charges or line power failures could be eliminated by a medical device having an alternative power source.

Also, an electrical medical device that operates without batteries or line power is advantageous for an emerging application for certain medical devices (such as defibrillators): "fire extinguisher" medical devices. Fire extinguisher defibrillators are located in places (e.g., wherever fire extinguishers are located) where they will be needed to provide easy and reliable operation, even by untrained personnel. Such defibrillators would be better served if there were no batteries to degrade over time or line power to fail. These defibrillators would thus not be affected by the battery or line power problems associated with smoke detectors.

Further, battery powered medical devices have disadvantages in foreign applications. For example, certain batteries may not be available in certain countries. Also, because of environmental laws, use and disposal of certain batteries is difficult. Further, battery rechargers and line power medical devices must be designed or adapted to use with the foreign power source.

Likewise, other mobile electrical medical devices would benefit from having a mechanical energy power source.

Accordingly, it would be advantageous to provide an alternate method of energizing medical devices. It would also be advantageous to provide a source of recharging the discharge capacitor of certain medical devices that eliminates the need for batteries and external battery charging. It would be further advantageous to not charge medical device's circuitry from stored electric power in a battery.

BRIEF SUMMARY OF THE INVENTION

One embodiment of the invention relates to a cardiac defibrillator for discharging an electrical charge into a patient. The cardiac defibrillator includes a device for storing mechanical energy, a generator, a capacitor, a charging circuit, a patient interface, an input device, and a control unit. The generator, coupled to the mechanical energy storage device, converts mechanical energy stored in the mechanical energy storage device into electrical energy. The charging circuit, coupled to the generator and the capacitor, transfers the electrical energy to the capacitor, wherein the electrical energy is stored in the capacitor. The patient interface, coupled to the capacitor and the patient, provides an electrical path for discharging the electrical energy stored in the capacitor into the patient. The input device generates a discharge signal. The control unit, coupled to the capacitor and input device, controls the discharge of the electrical energy into the patient in response to the discharge signal.

Another embodiment of the invention relates to a medical device configured to interface with a patient. The medical device comprises a device for storing mechanical energy and a generator. The generator, coupled to the mechanical energy storage device, converts mechanical energy stored in the mechanical energy storage device into electrical energy used to power the medical device.

Another embodiment of the invention relates to a method for powering a medical device by imparting potential mechanical energy into a mechanical energy storage device, converting the potential mechanical energy of the mechanical storage device into electrical energy with a generator, and powering the medical device using the electrical energy.

Another embodiment of the invention relates to a medical device including means for storing mechanical energy, means for converting the stored mechanical energy to electrical energy and control means coupled to the converting means for controlling the medical device.

Other principle features and advantages of the present invention will become apparent to those skilled in the art upon review of the following drawings, the detailed description, and the appended claims.

BRIEF DESCRIPTION OF THE DRAWINGS

The invention will become more fully understood from the following detailed description, taken in conjunction with the accompanying drawings, wherein like reference numerals denote like elements, in which.

DETAILED DESCRIPTION OF PREFERRED EMBODIMENTS

Although a medical device powered by electrical energy converted from mechanical energy could be one of several medical devices, described herein is a cardiac defibrillator. It would be understood that such an alternative power source could be used with other electrical medical devices, such as diagnostic electrocardiogram equipment.

Figure 1:
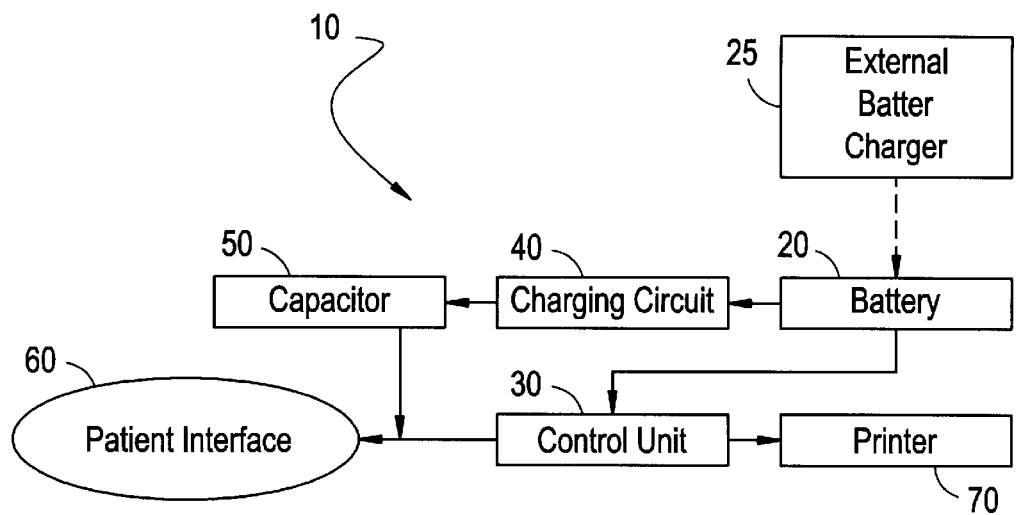
FIG. 1 is a block diagram showing the components of a conventional defibrillator.

Instead of using a battery to charge the cardiac defibrillator (as shown in FIG. 1), one embodiment of the invention includes a power supply that converts mechanical energy stored in a structure (such as a coil, spiral, or gas spring), to electrical energy to power the cardiac defibrillator capacitor. After a defibrillator operator inputs mechanical energy into the structure (e.g., stresses or winds the spring or compresses a gas), the mechanical energy is released to exert, preferably through a coupled gear mechanism, mechanical energy on a device (such as a dynamo) that converts the mechanical energy into electrical energy. The electrical energy is stored in the defibrillator's circuitry (such as by charging a capacitor). Such a feature eliminates the reliance on line power, or on an external battery charging apparatus or battery maintenance program, and because the defibrillator operator can stress the spring and recharge the capacitor in the field at any time, such a feature prevents the chance of having a defibrillator incapable of use due to a power line failure, or a weak or dead battery.

Figure 2:
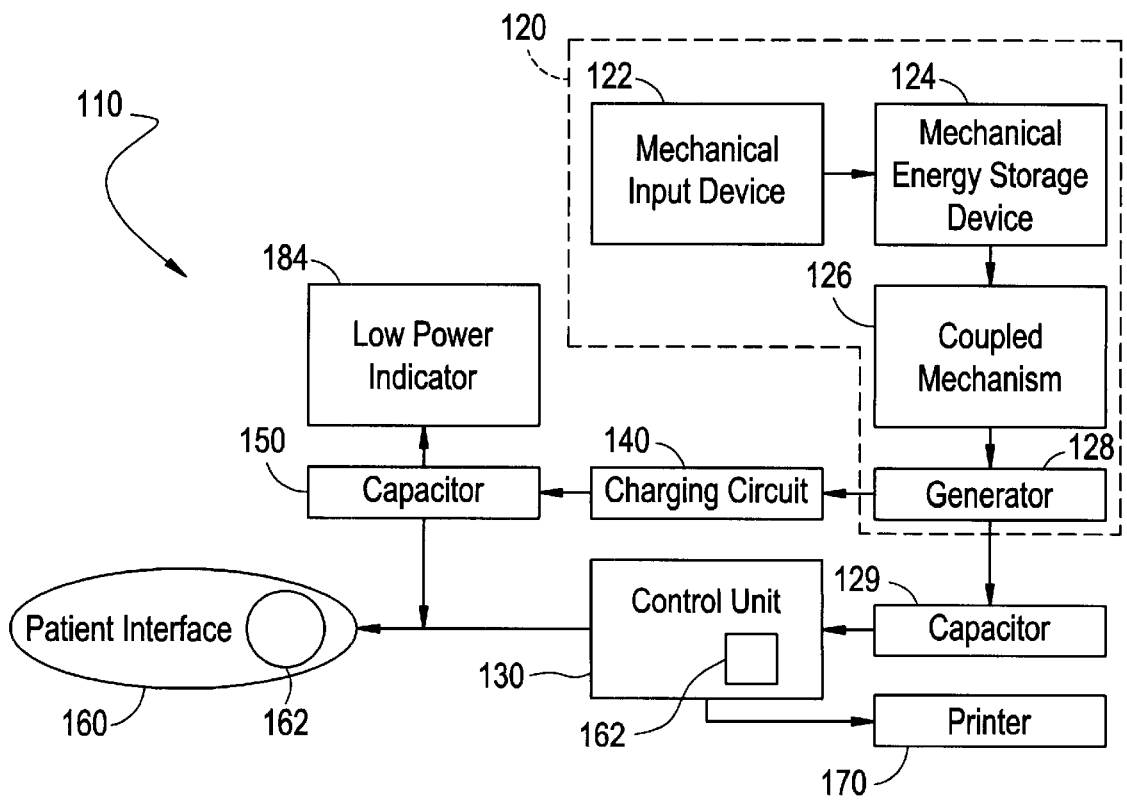
FIG. 2 is a block diagram showing the components of a first exemplary embodiment of a mechanically-powered defibrillator.

FIG. 2 shows the general arrangement of a defibrillator 110 including a generator assembly 120, a control unit 130, a charging circuit 140, a capacitor 150, and a patient interface 160.

Generator assembly 120 includes a mechanical input device 122 (such as a crank), a mechanical energy storage device 124, a coupled mechanism 126, and a generator 128. Mechanical input device 122 is operably coupled to mechanical energy storage device 124, which is coupled to generator 128, preferably through coupled mechanism 126. The input of mechanical power into mechanical energy storage device 124 using mechanical input device 122 can take a variety of embodiments. In an exemplary embodiment, a hand operated crank is used to stress a spring. As the spring unwinds, generator 128 is driven to provide a source of electrical energy for the defibrillator. In another embodiment, a foot actuated device compresses a spring, which subsequently decompresses and drives generator 128. In an exemplary embodiment, a hand pull-cord is used to provide rotational mechanical energy to generator 128. As the hand pull-cord is pulled, a shaft coupled to generator 128 rotates. The hand operated crank is preferred because a hand driven mechanism tends to be more reliable; that is, with the foot actuated device, the potential exists for damaging the device. The hand operated crank preferably includes a retractable crank with a handle (so during transport the handle is substantially flush mounted and is less susceptible to receiving blows).

Generator 128 is conventional and therefore all possible embodiments are not described in detail. Generally, one type of generator 128, a dynamo, includes a rotor and a stator. The rotor includes one or more magnets, and the stator includes a plurality of coil windings and substantially surrounds the rotor. In operation, coupled gear mechanism 126 rotates the rotor relative to the stator using power supplied by device 124. As the rotor rotates, the mechanical energy is converted to electrical energy.

When mechanical energy storage device 124 transmits mechanical energy to generator 128, the generator 128 converts the mechanical energy into electrical energy. Mechanical energy storage device 124, coupled mechanism 126, and generator 128 may be integrated together into a single arrangement, as conventionally known and available in the mechanical/electrical arts. In an exemplary embodiment, the generator assembly 120 includes a dynamo and a spring, wherein the defibrillator operator stresses and releases the spring by compressing it and allowing it to decompress or unwind. The decompressing spring actuates a coupled gear mechanism, which is coupled to the dynamo. The dynamo converts the rotation of the coupled gear mechanism to electrical energy. The spring may be one of a variety of spring types, including a spiral spring, a coil spring, a gas, or the like.

One type of generator assembly 120, a spiral spring dynamo, includes a spiral spring coupled to the shaft of a dynamo, a coupled mechanism connected to the shaft, and the dynamo. In the spiral spring dynamo, mechanical energy is stored in the spiral spring by rotating a shaft (e.g., by a crank, knob, or the like) coupled to the spiral spring. A stop pin may be included on the shaft to prevent overrotation of the spiral spring. When the stressed, spiral spring is released, and allowed to return to its unstressed state, the coupled mechanism is operably engaged. Though the shaft may be coupled directly to the dynamo, the coupled mechanism may be comprised of one or more gears for maximum mechanical advantage and efficiency. In an exemplary embodiment, the dynamo includes a flywheel operably coupled to the coupled drive. Thus, rotation of the flywheel rotates the rotor, thus electric energy is produced.

In another type of generator assembly 120, a coil spring dynamo, the mechanical energy is stored in a coil spring when the coil spring is stressed (i.e., compressed or stretched) by a button, lever, foot pedal, or the like. When the stressed, coil spring is released to return to an unstressed state, a coupled gear mechanism rotates the flywheel of the dynamo. The coupled gear mechanism can be actuated by a rack and pinion gear coupled to the coil spring, or the like. As the coil spring returns to a unstressed state, the rack and pinion induces rotation of the coupled gear mechanism.

In another type of generator assembly 120, a gas spring dynamo, the mechanical energy is stored is a chamber when a gas (such as air) is compressed by a pump actuator, foot pedal, lever, or the like. When the compressed gas is released, the coupled mechanism is actuated to drive the generator.

Defibrillator 110 further includes a second capacitor 129. The output of generator 128 is also used to charge second capacitor 129, which is used to power control unit 130. Control unit 130 is configured to control the operation of defibrillator 110 and provide the defibrillator operator a display (not shown) to view. Control unit 130 is electrically coupled to patient interface 160 and capacitor 150. When the defibrillator operator instructs defibrillator 110 to deliver the charge to the patient, control unit 130 signals capacitor 150 to pass the stored charge to the patient through patient interface 160.

Charging circuit 140 transfers the electrical charge from generator assembly 120 to capacitor 150. Capacitor 150 and control unit 130 are electrically coupled to patient interface 160. Capacitor 150 holds the charge until control unit 130 instructs the charge be delivered or discharged into a patient through patient interface 160. Patient interface 160 usually includes either pads, paddles, or internal spoons that physically contact to the patient. In a medical device other than a defibrillator, the patient interface could be configured to interface or communicate with the patient.

In an exemplary embodiment, defibrillator 110 further includes a printer 170 which is electrically coupled to control unit 130 and is used to output a hard copy of rhythm strips and textual information. Such output is then reviewed by the defibrillator operator while treating the patient.

Defibrillator 110 further includes an input device 162 which is configured to provide the defibrillator operator with an interface to operate defibrillator 110. Input device 162 is adapted to signal the defibrillator to discharge or to output information to printer 170. Input device 162 may be operator actuatable or automatically actuatable. When input device 162 is operator-actuatable, the defibrillator operator physically actuates input device 162. When the defibrillator operator actuates input device 162 and instructs defibrillator 110 to deliver the charge to the patient, control unit 130 signals capacitor 150 to pass the stored charge to the patient through patient interface 160. Examples of operator-actuatable input device 162 include buttons on patient interface 160 (e.g., when paddles or internal spoons are being used), or buttons on control unit 130 (e.g., when pads are being used). When input device 162 is automatically-actuatable, control unit 130 includes a conventionally known device that triggers the input device if the condition of the patient warrants. Such devices are intended to operate "automatically," i.e., without direct defibrillator operator control. In a medical device other than a defibrillator, the input device could be configured to signal the medical device to perform a function, such as actuate a mechanism, take a measurement, run a diagnostic analysis, interface or communicate with the patient, or the like.

In operation, the defibrillator operator exerts energy on mechanical energy storage device 124 using mechanical input device 122 (e.g., winds a spring to a predetermined point). As mechanical energy storage device 124 releases the stored mechanical energy (e.g., unwinds), generator 128 converts the mechanical energy to electrical energy.

After mechanical energy is applied to mechanical energy storage device 124, it may be immediately released for use, or it may be stored by mechanical energy storage device 124 for release at a later time. Because the time it takes to exert mechanical energy on mechanical energy storage device 124 (e.g., wind and release the spring) is minimal, the defibrillator is generally left in an uncharged and unwound state. The electrical power of generator 128 is passed to charging circuit 140 which steps up the voltage as necessary to charge capacitor 150 that is used to deliver the charge to the patient.

Figure 3:
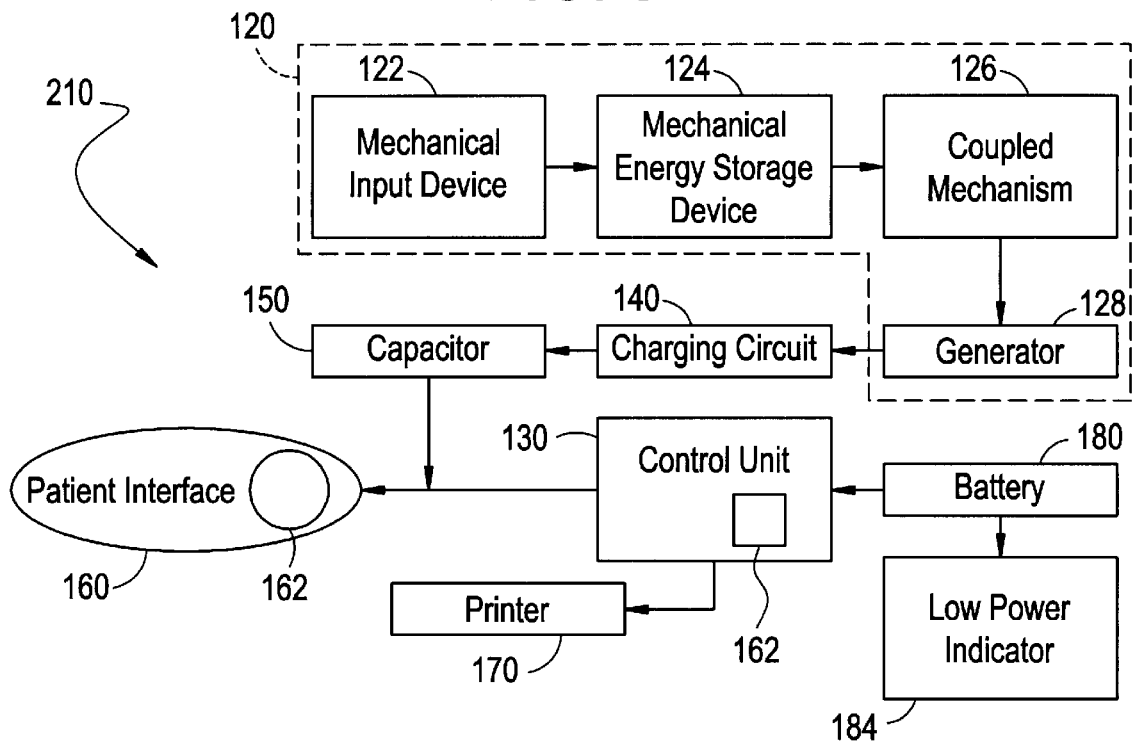
FIG. 3 is a block diagram showing the components of a second exemplary embodiment of a mechanically-powered defibrillator.

Another exemplary embodiment, as shown in FIG. 3, illustrates the general arrangement of a defibrillator 210, which is partially powered by a battery 180. The defibrillator 210 includes a generator assembly 120, a control unit 130, a charging circuit 140, a capacitor 150, a patient interface 160, and a printer 170. Control unit 130, charging circuit 140, capacitor 150, patient interface 160, and printer 170 operate substantially the same as described in FIG. 2 and so are identified by similar reference numerals.

Defibrillator 210 primarily uses generator assembly 120 to power the operation of the system. Generator assembly 120 includes mechanical input device 122, a mechanical energy storage device 124, coupled mechanism 126, and a generator 128. Mechanical energy storage device 124 is coupled to generator 128 such that when the mechanical energy in mechanical energy storage device 124 is released (e.g., when a spring is allowed to decompress or unwind), the mechanical potential energy is converted by generator 128 into electrical energy. Mechanical energy storage device 124 and generator 128 arrangement is conventionally known and available in the art of mechanical/electrical power conversion.

The output of generator 128 provides electrical energy to charging circuit 140. Charging circuit 140 transfers the electrical charge from generator assembly 120 to capacitor 150. Capacitor 150 is electrically coupled to patient interface 160. Capacitor 150 holds the charge until control unit 130 instructs the charge to be delivered or discharged into a patient through patient interface 160. Patient interface 160 usually includes either pads or paddles that are physically connected to the patient.

Instead of control unit 130 being powered by generator assembly 120 (as shown in FIG. 2), control unit 130 is powered by one or more batteries 180. Preferably, battery 180 is a small conventionally available disposable or rechargeable type (e.g., 9-volt or double-A (i.e., AA)). Battery 180 is electrically coupled to low battery indicator 184.

Low power indicator 184 is conventionally available and is configured to signal the defibrillator operator that battery 180 has a low charge. In a medical device other than a cardiac defibrillator, low power indicator 184 is configured to signal the operator that the stored electrical energy, which had been converted from mechanical energy, is low. Low power indicator 184 signals the operator by a flashing light or a conventional "chirp" circuit to draw attention to the operator that the stored electrical energy is low or that battery 180 needs to be replaced. When low power indicator 184 indicates that battery 180 has a low charge, battery 180 is replaced or recharged. When low power indicator 184 indicates that the stored electrical energy is low, mechanical input device is actuated and generator 128 converts the mechanical energy to electrical energy.

In an exemplary embodiment, printer 170 is electrically coupled to control unit 130 and is used to output a hard copy of rhythm strips and textual information.

Figure 4:
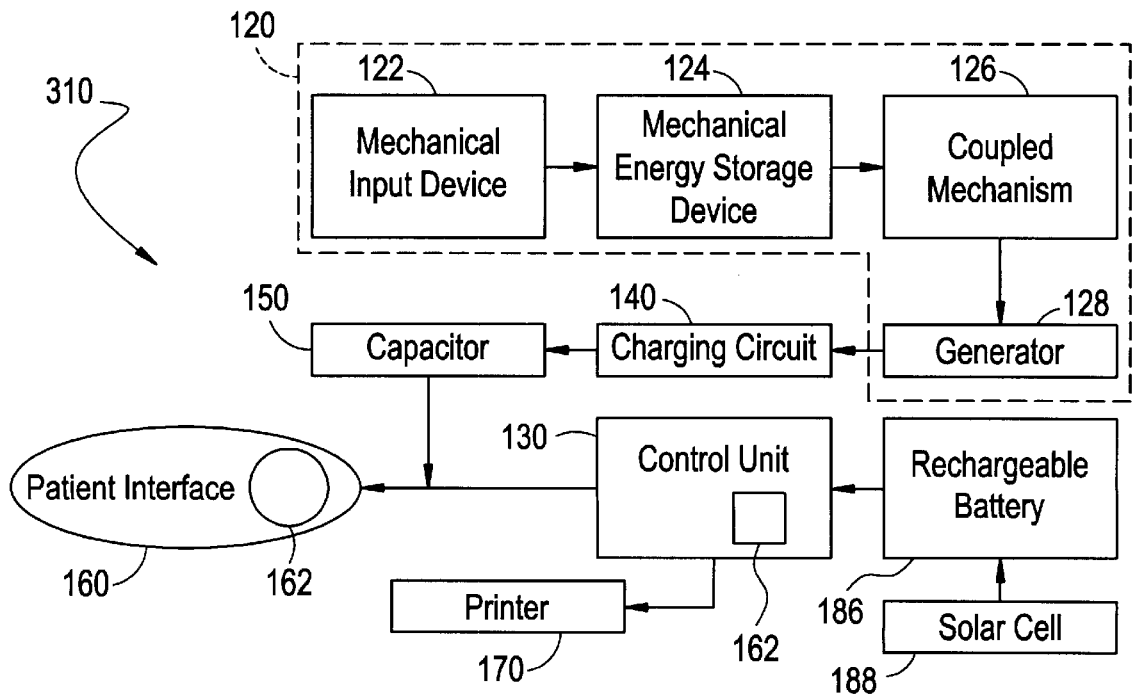
FIG. 4 is a block diagram showing the components of a third exemplary embodiment of a mechanically-powered defibrillator.

In another exemplary embodiment, FIG. 4 shows the general arrangement of a defibrillator 310 wherein the defibrillator is partially powered by a solar power-rechargeable battery 186. Defibrillator 310 includes a generator assembly 120, a control unit 130, a charging circuit 140, a capacitor 150, a patient interface 160, and a printer 170. Control unit 130, charging circuit 140, capacitor 150, and patient interface 160 operate substantially the same as described in FIG. 2 and so are identified by similar reference numerals.

Defibrillator 310 primarily uses generator assembly 120 to power the operation of the system and includes mechanical input device 122, a mechanical energy storage device 124, a coupled mechanism 126, and a generator 128. Mechanical energy storage device 124 is coupled to generator 128 such that when stored mechanical energy of mechanical energy storage device 124 is released (e.g., a spring is allowed to decompress or unwind), the mechanical energy is converted by generator 128 into electrical energy. The electrical energy is stored in capacitor 150 until it is discharged into the patient through patient interface 160.

The energy output of generator 128 provides electrical energy to charging circuit 140. The charging circuit 140 stores the electrical charge from generator assembly 120 in capacitor 150, which is electrically coupled to patient interface 160. Capacitor 150 holds the charge until control unit 130 instructs patient interface 160 to deliver or discharge into a patient. Patient interface 160 usually includes either pads or paddles that are physically connected to the patient.

Instead of control unit 130 being powered by generator assembly 120 (as shown in FIG. 2) control unit 130 is powered by rechargeable battery 186. Preferably, rechargeable battery 186 is embedded in control unit 130. Whether rechargeable battery is embedded or not, rechargeable battery 186 can be recharged by any conventional means. As shown in FIG. 4, rechargeable battery 186 is charged by solar cell 188 that uses the ambient light as a power source In an exemplary embodiment, printer 170 is configured to output a hard copy of rhythm strips and textual information. Printer 170 is electrically coupled to rechargeable battery 186 through control unit 130.

Because batteries are the number one source of failure with defibrillators, using a mechanical-to-electrical energy converting assembly as disclosed herein solves this industry-wide problem. Also, batteries used for defibrillators require daily maintenance and testing. Further, because batteries are not standard, replacement batteries can be difficult to obtain. Thus, the disclosed energy converting assembly eliminates the need for replacement of batteries that operate a defibrillator and for external battery chargers. Also, in-hospital defibrillators no longer need to be continuously plugged in. Further, the patient receives better care because there is no limit on the number of discharges that can be delivered; that is, the device will not fail due to a weakened or dead battery. Field applications, such as military or civilian humanitarian, often take place far from a source of reliable power. Because the battery charging step is eliminated, and AC line power is not needed, the mechanically-powered defibrillator can be deployed anywhere.

Besides conventional applications, the energy converting defibrillator is important for an emerging defibrillator application. In addition to in-hospital and pre-hospital applications, there is a movement to deploy so-called "fire extinguisher" defibrillators, i.e., small defibrillators that can be deployed anywhere (e.g., everywhere a fire extinguisher is present). Because studies indicate that only 5%–10% of the people who could benefit from defibrillation actually receive treatment in time, a defibrillator that is immediately assessable and requires minimum maintenance is needed. A dynamo powered defibrillator can sit on the shelf before being used with the potential for battery failure being reduced or eliminated.

While the embodiments illustrated in the FIGURES and described above are presently preferred, it should be understood that these embodiments are offered by way of example only. Other embodiments may include, for example, various configurations of mechanical input devices, mechanical storage devices, coupled mechanisms (or elimination thereof), generators, spring dynamo assemblies, or defibrillators. Moreover, although a cardiac defibrillator was described by way of an example, it should be understood that an apparatus that converts mechanical energy to electrical energy could be used in other medical devices that operate on electrical energy. The invention is not limited to a particular embodiment but extends to various modifications, combinations, and permutations that nevertheless fall within the scope and spirit of the appended claims.

What is claimed is:

1. A cardiac defibrillator for discharging an electrical charge into a patient, comprising:
    a mechanical energy storage device adapted to be located external to the patient;
    a generator coupled to the mechanical energy storage device and configured to convert mechanical energy stored in the mechanical energy storage device into electrical energy wherein the electrical energy converted by the generator from the mechanical energy stored in the mechanical energy storage device provides the electrical charge for discharging into the patient;
    an electrical charge storage device adapted to store the electrical energy;
    a charging circuit coupled to the generator and configured to transfer the electrical energy to the electrical charge storage device;
    a patient interface adapted to be coupled to the charging circuit and the patient and configured to provide an electrical path for discharging the electrical charge;
    an input device configured to generate a discharge signal;
    a control unit coupled to the electrical charge storage device and the input device and configured to control the discharge of the electrical charge into the patient in response to the discharge signal;
    wherein the electrical energy converted by the generator from the mechanical energy is stored in the electrical charge storage device so that the electrical charge is dischargeable into the patient through the patient interface upon operation of the input device.

2. The cardiac defibrillator of claim 1, wherein the mechanical energy storage device includes a spring.

3. The cardiac defibrillator of claim 2, wherein the spring is one of a coil spring, a spiral spring, and a pneumatic spring.

4. The cardiac defibrillator of claim 1, further including a mechanical input device for providing the mechanical energy to the mechanical storage device.

5. The cardiac defibrillator of claim 4, wherein the mechanical input device is one of hand-actuated and foot-actuated.

6. The cardiac defibrillator of claim 1, wherein the patient interface is adapted to be located external to the patient during discharge of the electrical charge.

7. The cardiac defibrillator of claim 1, further including a low power indicator which generates a signal when the defibrillator is low on electrical energy.

8. The cardiac defibrillator of claim 1, further including a battery configured to power the control unit.

9. The cardiac defibrillator of claim 8, further including a low power indicator coupled to the battery.

10. The cardiac defibrillator of claim 8, further including a solar cell which recharges the battery.

11. A medical device configured to interface with a patient, the medical device comprising:
    a mechanical energy storage device;
    an externally operated mechanical input device operatively coupled to the mechanical energy storage device;
    a generator coupled to the mechanical energy storage device and configured to convert mechanical energy stored in the mechanical energy storage device into electrical energy used to power the medical device;
    an electrical charge storage device adapted to store the electrical energy;
    wherein the electrical energy converted by the generator from the mechanical energy stored in the mechanical energy storage device and stored in the electrical charge storage device provides the electrical charge for discharging into the patient.

12. The medical device of claim 11, further comprising:
    an input device configured to generate a signal; and
    a control unit coupled to the input device and configured to control the medical device in response to the input device signal.

13. The medical device of claim 11, wherein the medical device is one of a cardiac defibrillator, an electrocardiograph, ambulatory electrocardiograph, and a transport monitor.

14. The medical device of claim 11, wherein the mechanical energy storage device includes a spring.

15. The medical device of claim 14, wherein the spring is one of a coil spring, a spiral spring, and a pneumatic spring.

16. The medical device of claim 11, wherein the device for storing mechanical energy is adapted to be located external to the patient.

17. The medical device of claim 11, wherein the mechanical input device is one of hand-actuated and foot-actuated.

18. The medical device of claim 11, further including a coupled mechanism coupling the mechanical energy storage device and the generator.

19. The medical device of claim 11, further including a low power indicator which generates a signal when the medical device is low on electrical energy.

20. The medical device of claim 12, further including a battery configured to power the control unit.

21. The medical device of claim 20, further including a low power indicator coupled to the battery.

22. The medical device of claim 20, further including a solar cell which recharges the battery.

23. A method for powering a medical device comprising the steps of:
    providing a mechanical energy storage device adapted to be external to a patient, a generator, an electrical energy storage device;
    imparting potential mechanical energy into the mechanical energy storage device adapted to be external to a patient;
    converting the potential mechanical energy of the mechanical energy storage device into electrical energy with the generator;
    storing the electrical energy in the electrical energy storage device; and
    powering the medical device using the electrical energy that was converted from the mechanical energy.

24. The method of claim 23, further including powering a control unit with a battery.

25. The method of claim 24, further including recharging the battery with a solar cell.

26. The method of claim 23, further including monitoring the electrical energy with a low power indicator.

27. A medical device, comprising:
    a power source operable external to a living body and configured to power the medical device, the power source including:

means for generating mechanical energy adapted to be external to a living body;

means for storing mechanical energy;

means for converting the stored mechanical energy to electrical energy;

means for storing the electrical energy; and means for controlling the medical device coupled to the means for converting the stored mechanical energy to electrical energy and means for storing the electrical energy;

wherein the electrical energy converted by the means for converting the stored mechanical energy to electrical energy from the mechanical energy stored in the means for storing mechanical energy and stored in the means for storing electrical energy provides the electrical charge for powering the medical device.

28. The medical device of claim 27, wherein the means for converting the stored mechanical energy to electrical energy includes a generator and the means for storing mechanical energy includes a mechanical energy storage device, wherein the generator converts mechanical energy from the mechanical energy storage device into electric energy.

29. The medical device of claim 27, further including means for discharging the electrical energy and a patient interface means for providing an electrical path for the electrical energy to a patient.

30. The medical device of claim 29, further including a charging circuit coupled to the means for converting the stored mechanical energy to electrical energy, wherein the means for storing the electrical energy is coupled to the patient interface means and the charging circuit is coupled to the means for storing the electrical energy, the charging circuit being configured to transfer the electrical energy to the means for storing the electrical energy.

31. The cardiac defibrillator of claim 1, wherein the input device is configured to generate a single discharge in response to a single discharge signal.

32. The cardiac defibrillator of claim 31, wherein the single discharge signal is generated from a single manual operation of the input device.

33. The medical device of claim 12, wherein the input device is configured to generate a single discharge in response to a single discharge signal.

34. The medical device of claim 33, wherein the single discharge signal is generated from a single manual operation of the input device.

35. The medical device of claim 23, further comprising generating a single discharge of the electrical energy in response to a single manual operation of an input device.

* * * * *